(12) United States Patent
Kumar et al.

(10) Patent No.: US 7,470,832 B2
(45) Date of Patent: Dec. 30, 2008

(54) IN-VITRO SYSTEM OF MICROPROPAGATION OF ROSE SCENTED PELARGONIUM GRAVEOLENS, OF BOURBON TYPE

(75) Inventors: Anil Kush Kumar, Maharashtra (IN); Debasis Patnaik, Orissa (IN)

(73) Assignee: Reliance Life Sciences Pvt. Ltd., Maharashtra (IN)

(*) Notice: Subject to any disclaimer, the term of this patent is extended or adjusted under 35 U.S.C. 154(b) by 224 days.

(21) Appl. No.: 10/453,016

(22) Filed: Jun. 3, 2003

(65) Prior Publication Data

US 2005/0076413 A1   Apr. 7, 2005

Related U.S. Application Data

(60) Provisional application No. 60/385,288, filed on Jun. 3, 2003.

(51) Int. Cl.
*A01N 63/00* (2006.01)
*A01H 3/00* (2006.01)

(52) U.S. Cl. .................. 800/295; 504/117; 47/58.1

(58) Field of Classification Search ................. 800/295; 504/117; 47/58.1
See application file for complete search history.

(56) References Cited

OTHER PUBLICATIONS

Gupta et al. Micropropagation of Elite Cultivars of Rose-scented Geranium (*Pelargonium graveolens* L' Herit.) for industrial Production of Propagules 2002 Indian Journal of Biotechnology pp. 286-291.*

Smith Roberta H. Plant Tissue Culture. 2000. Techniques and experiments second edition. Academic Press. 43-58, 70-81.*

Arockiasamy D. I. et al. Plant regeneration from node and Internode Explants of Solanum triblobatum I. 2002. Plant Tissue Cult. 12(2): 93-97.*

Arockiasamy et al. Plant Regeneration from Node and Internode Explants of Solanum Trilobatum L. Plant Tissue Cult. 12(2)2002.*

Saxena et al. Composition of the essential oil of a New Isomenthone-Rich variant of geranium Obtained from Geraniol-Rich Cultivar of *Pelargonium* Species. Journal of essential Oil Research Mar./Apr. 2004. Abstract.*

Perez et al. Micropropagation of fazinus angustifolia from mature and juvenile plant material. Plant Cell, Tissue and Organ Culture 37: 297-302 1994.*

* cited by examiner

*Primary Examiner*—Annette H Para
(74) *Attorney, Agent, or Firm*—J. Harold Nissen; Lackenbach Siegel, LLP

(57) ABSTRACT

A highly efficient in-vitro system of micropropagation of rose scented Geranium, *Pelargonium graveolens* L. Herit by a direct regeneration method to produce a large number of viable true to the type plants maintaining the genotype of an elite mother plant is provided. The process involves inoculating nodal explants on shoot regeneration and multiplication medium, transferring the multiple shots for further growth on medium for shoot growth, further transferring the shoot with sufficient growth to medium for rooting. The present invention also provides a process for the primary and secondary hardening of the in vitro generated plants with the efficient root regeneration system, which is hardened to give about 95% survival in the field conditions. The multiplication ratio achieved by the process is of the order of 1:12-1:20, resulting in significantly low cost of production in relatively lesser time.

18 Claims, 1 Drawing Sheet

FIGURES:
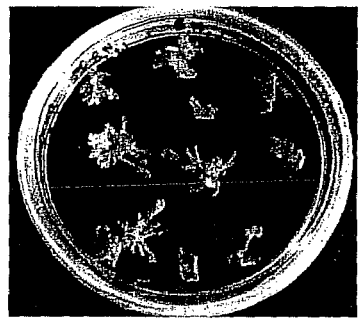
Figure 1: Initiation of callus from leaf ex-plant
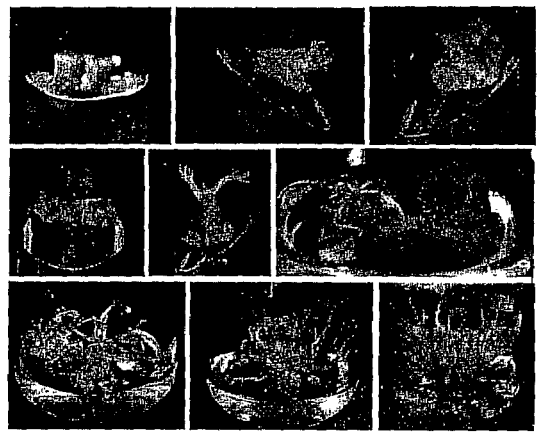
| a | b | c |
| d | e | f |
| g | h | I |
Figure 2: Whole Process of Micropropagation From Nodal Explant.

IN-VITRO SYSTEM OF MICROPROPAGATION OF ROSE SCENTED PELARGONIUM GRAVEOLENS, OF BOURBON TYPE

CROSS-REFERENCE TO RELATED APPLICATION

This Application claims priority from U.S. Provisional Patent Application Ser. No. 60/385,288 filed Jun. 3, 2002, entitled:

This Application also includes information with respect to protection for a plant and separate protection will be sought for the novel plant disclosed in this Application and in the basic provisional application.

Color drawings in addition to black and white drawings are being submitted with this Application.

FIELD OF THE INVENTION

The present invention relates to a highly efficient in-vitro system of micropropagation of rose scented Geranium, *Pelargonium graveolens* L. Herit of Bourbon type to produce large number of viable plants.

BACKGROUND OF THE INVENTION

Geranium is a native of the Cape Province in South Africa. It is commercially cultivated in France, Belgium, Spain, Morocco, Madagascar, Egypt, Reunion Islands, Congo, China, former USSR countries and to some extent in India and Israel for the production of the oil.

*Pelargonium graveolens* commonly known as Rose-scented *Pelargonium,* Rose-scented geranium or Rose geranium, is one of the many fragrant species of *Pelargonium,* belonging to the family Geraniaceae. *Pelargonium graveolens* is an erect, much-branched shrub with its attractive, strongly rose-scented leaves. The genus *Pelargonium* gets is name from the resemblance of the shape of the fruit to the beak of a stork, *pelargos* in Greek. The species name *graveolens* refers to the strong fragrance of the leaves, *graveolens* meaning strong-smelling in Latin.

*Pelargonium graveolens* is used in the production of geranium oil, which has a delightful floral fragrance, which makes it very pleasing to most people, and is highly priced for its very profound and strong rose like odour.

The oil of geranium, almost a perfume by itself, is stable and blends well with other fragrances lavender, patchouli, clove, rose, sandalwood, jasmine, juniper, neroli, bergamot and other citrus oils. It is widely used in perfumery and cosmetic products, and for the isolation of rhodinal, which forms part of most high-grade perfumes. It is also used as a substitute for the expensive scented oil of roses in the perfume trade. It's often used to scent soaps and detergents because, unlike many other essential oils, rose geranium's aroma profile is not readily affected by the alkaline nature of soap products.

There are several types of geranium oil, the main ones being Reunion or Bourbon, Algerian, Moroccan, and French. Reunion oil is very rich in citronellol and has a heavy rose and minty odor. Algerian oil has a delicate odor. Moroccan oil is similar to Algerian oil. French oil is thought to possess the finest rose-like odor. The concrete and absolute of geranium are also available commercially. Bourbon is considered the finest type, which is produced from the Rose Geranium, which is a hybrid of *P. radens* and *P. capitatum.* The name comes from the island, and the former French colony of La Réunion (previously known as Île de Bourbon), 800 km east of Madagascar, in the Indian Ocean. The island has the ideal climate and soil conditions for production of geranium. Bourbon geranium is cultivated and distilled exclusively on the island. The environment of Reunion has produced a strain of geranium with a very rich, rosy aroma. The geranium oil produced in other parts of the world may originate from different species.

The oil is composed chiefly of geraniol, citronellol, linalool, citronellyl formate. The oil also contains $\alpha$-pinene, $\beta$-pinene, $\alpha$-terpniene, myrcene, $\alpha$-phellandrene, limonene, cis-ocimene, trans ocimene, p-cymene, terpinolene, cis-rose oxide, trans-rose oxide, menthone, trans-linalool, iso-menthone, carvophyllene, geranyl acetate, nerol, and geranyl formate, geranyl butyrate. However the chief constituent of the geranium oil is geraniol and citronellol. The citronellol: geraniol ratio is considered to be a distinguishing factor of the essential oil type that determines the quality of perfume. The Bourbon type of Reunion origin, the best quality commercial Geranium oil, has almost equal quantity of the Citronellol and Geraniol.

The essential oil is steam distilled from the leaves, stalks and flowers. The plant should be cut just before the flowers open and between 300 and 500 kg of plant material is required in order to obtain about 1 kg of essential oil. Most of the essential oil glands are found in its leaves. After cutting, the plants are partially dried to increase the yield of oil leaving less water to be vaporized and extracted from the plant material during the distillation. The essential oil in rose geranium leaves has the constituents, geraniol, linalool and citronellol, which are also present in rose oil. The well-balanced aroma of geranium's fragrance resembles that of rose with a musty, minty-green undertone.

In addition to its use in perfumery and cosmetics it also has pharmaceutical uses. The oil is non-toxic, non-irritant and generally non-sensitizing. It is reported to have a strong strengthening effect, effective in balancing emotions, raise energy reserves while soothing the mind and body. It is also described to balances sebum and therefore can suitable for all skin types.

The oil is also extensively used as a flavoring agent in most major food categories, alcoholic beverages and soft drinks.

The world production of geranium oil is estimated at 250-300 tonnes, whereas the demand is more than 800 tonnes annually. In India the requirement of oil is about 140 tonnes per year, whereas India is able to produce a meager quantity of about 5 tonnes geranium oil per year. As the production of Geranium oil is inadequate to meet the growing demand of the Indian perfumery Industry, the oil is met mainly by imports. Taking into consideration the high demand of this oil for cosmetic and perfumery industries in Indian as well world over, there is a large scope for the cultivation of this important plant in India.

Besides the use of *Pelargonium graveolens* plants as a source of essential oil, it is also cultivated for its floriculture value as well as for medicinal purpose. As a medicinal plant, geranium has traditionally been considered an astringent and used as a folk remedy in the treatment of ulcers. A terpine hydrate synthesized from geraniol is known to be an effective expectorant. Leaves are reported to have antifungal activity. Geranium is reported to repel insects because of its citronellol content.

Of late, the plant has also shown to have great potentials in phyto-remediation. The term "phyto-remediation" refers to an innovative technology that uses plants to remove and/or degrade environmental contaminants such as heavy metals and organic compounds. *Pelargonium graveolens* has been shown to tolerate high level of lead, copper and various hydrocarbon toxicity in soil.

From the foregoing thus it is apparent that either for the production of oil for various industries or the applications of *Pelargonium graveolens* for other various purposes, there is a huge demand for *Pelargonium graveolens* plants, which necessitates its large-scale cultivation.

*Pelargonium graveolens* is conventionally propagated by means of stem cuttings, or seed. The vegetative propagation by cuttings however, suffers from major disadvantages like relatively low numbers of plant multiplication, possibility of systemic pathogens getting propagated as well, limited time period during which plant can be multiplied, and relative high mortality.

Moreover propagation from seeds could change the genetic composition of the plant, which can cause undesirable changes with respect to its oil composition or yield. Which could make it unsuitable as a source of oil for perfumery or cosmetic or pharmaceutical industry for which it is chiefly cultivated.

The afore mentioned barriers associated with large scale propagation of *Pelargonium graveolens* can be overcome by in-vitro regeneration using micropropagation technique like tissue culture.

Micropropagation can be defined as in-vitro regeneration of plants from organs, tissues, cells or protoplast using technique like tissue culture for developing true-to type resultant plants of a selected genotype. In general tissue from a plant commonly known as explant, is isolated from a plant whose multiplication is desired to create a sterile tissue culture of that species in-vitro. From explant a culture is initiated, once a culture is stabilized and growing well in-vitro, multiplication of the tissue or regeneration of entire plant can be carried out. Shoots (tips, nodes or internodes) and leaf pieces are commonly used but cultures can be generated from many different tissues. Juvenile tissues generally respond best. Besides explant the chemical composition of the culture medium and the physical environment of cultures have been found to be of a great influence on the regeneration capacity, multiplication ration, growth and development of new plants in the culture system. Therefore one needs to optimize these factors for individual plant species.

Plant tissue culture is rapidly becoming a commercial method for large-scale propagation of the elite varieties, for plants difficult-to-propagate rapidly by conventional methods. Tissue culture is particularly useful for multiplication of plants, which are slow growing (turmeric, ginger, cardamom); cross-pollinated (coconut, teak, eucalyptus, cashew, mango and those which show wide variation in the progeny), male sterile lines (cotton, sorghum, pearl millet); newly free plants by meristem culture (sugarcane, potatoes, tapioca, etc).

Some work has been reported for micropropagation of different species of *Pelargonium* using tissue culture techniques. For instance U.S. Pat. No. 5,514,580 granted to Oglevee-O'Donovan et al. For "In vitro leaf petiole multiplication of *Pelargoniums*" describes a process for propagating *Pelargonium domesticum* varieties by tissue culture propagation of petiole sections taken from a mother plant. Wherein the effectiveness of the process at least in part is attributed to growth regulator selected from amino or benzyl—glucoside or glycoside the exemplary being benzylamino riboside.

However very limited work has been attempted for micropropagation of *Pelargonium graveolens*.

For example study carried out by P. V. Lakshmana Rao, for in vitro plant regeneration of scented-leaved geranium *Pelargonium graveolens*, cited in Plant Science, Volume 98 (2), 193-198, 1994, discloses regeneration of plants from leaf segments involving callus formation on medium supplemented with 5 microM each of NAA, 2,4-D and 2.5 microM Kinetin and transferring of the primary callus to MS medium supplemented with 20 microM 2-isopentyl adenine, 10 microM kinetin and 108 microM indole-3-butyric acid or phloroglucinol for shoot regeneration. It is well known to those skilled in the art that the micropropagation method involving callus formation may not give true to type clones due to the possibility of somaclonal variation during callus formation. Moreover such indirect process would involve additional step of regeneration from callus and also additional media, therefore such process may not be very cost effective and also would be lengthy and time consuming.

Another study reported in Plant Science 155 (2000), 133-140, by Saxena Gauri, et al., describes an efficient in vitro procedure for micropropagation and generation of somaclones of rose scented *Pelargonium graveolens* Indian cultivar Hemanti of Algerian type. As reported the study involves direct and indirect regeneration of shoots from leaf and nodal explants. The best media reported for direct regeneration are, MS medium supplemented with 5 mg per liter of kinetin and 1 mg per liter of NAA for leaf explant, MS medium supplemented with 8 mg per liter of kinetin and 1 mg per liter of NAA for nodal explant and for indirect regeneration for nodal explants MS medium supplemented with 10 mg per liter kinetin and 1 mg per liter of NAA giving rise to callus formation. The rooting is carried out on half strength MS medium with 1 mg per liter of IBA. The study is however associated with certain drawbacks like it does not provide protocol for in vivo acclimatization of direct regenerated plants. Besides the main basis of the study is to develop somaclonal variants with the objective of extending area of cultivation beyond the conventional habitat, whereas the acclimatization of callus derived somaclones is provided limiting only to the north Indian plains and does not encompass the acclimatization in other geographical area with varied geographical conditions. Furthermore study is restricted only to Algerian variety.

As evident from above, of whatever limited work carried out on micropropagation of *Pelargonium graveolens* none of the studies are directed specifically towards Bourbon or Reunion type, which has high demand in commercial market for the fine premium quality of its oil. Therefore there remains the need to develop a highly efficient system for rapid multiplication of rose scented geranium *Pelargonium graveolens* of Bourbon or Reunion type by in-vitro micropropagation, which is devoid of drawbacks associated with prior arts, which can provide true to type resultant plants to maintain the genotype of the elite variety and give rise to large number of the planting material rapidly by cost effective method for the said genotype.

OBJECTS OF THE INVENTION

Accordingly it is an object of the present invention to provide a highly efficient in-vitro system for micro-propagation of rose scented geranium *Pelargonium graveolens* L. Herit of Bourbon or Reunion type.

It is also an object of the present invention to provide a highly efficient in-vitro system for micro-propagation of rose scented geranium *Pelargonium graveolens* L. Herit of Bourbon or Reunion type with high multiplication-ratio.

It is still an object of the present invention to identify the explant, media and culture conditions for producing large number rose scented geranium *Pelargonium graveolens* L. Herit of Bourbon or Reunion type.

It is yet another object of the present invention to provide economically viable-highly efficient in-vitro system for micro-propagation of rose scented geranium *Pelargonium graveolens* L. Herit of Bourbon or Reunion type.

It is further object of the present invention to provide a highly efficient in-vitro system for micro-propagation of rose scented geranium *Pelargonium graveolens* L. Herit of Bourbon or Reunion type.

It is further object of the present invention to provide a highly efficient in-vitro system for micro-propagation of rose scented geranium *Pelargonium graveolens* L. Herit of Bourbon or Reunion type by direct regeneration method conserving the elite plant genotype.

It is further object of the present invention to provide a process for the primary and secondary hardening of the in vitro generated plants producing large number of healthy viable plants of rose scented geranium *Pelargonium graveolens* L. Herit of Bourbon or Reunion type.

SUMMERY OF THE INVENTION

A highly efficient in-vitro system of micropropagation of rose scented Geranium, *Pelargonium graveolens* L. Herit of Bourbon or Reunion type by direct regeneration method to produce large number of viable true to the type plants maintaining the genotype of an elite mother plant is provided.

The present invention process for in-vitro system micro-propagation of rose scented geranium *Pelargonium graveolens* L. Herit, comprises of, deriving various explants from mother plants of desired characteristics growing in green house conditions for at least 4 months; cleaning & surface sterilizing the explants; inoculating the explants on medium for shoot regeneration and multiplication comprising of modified MS medium supplemented with auxins like NAA 0.05-5 mg per liter, cytokinins like kinetin 2.5-7.5 mg per liter or BAP 0.15-3 mg per liter, or the like and or combination thereof, inositol 200-400 mg per; incubating the inoculated explants for a photoperiod of day with 24 hours of night or dark period for period of 2-10 days at a temperature of 18-25 degree centigrade; relocating the cultures to growth room with light intensity of about 60-80 .mu.mol m.sup.−2s.sup−1 having about 10-20 hours of light daily; at 18-25° C. temperature for at least 3-6 weeks to give healthy cultures; harvesting the multiple shoots with the healthy growth; dissecting the multiple shoots into 0.2-1 cm size and transferring to a medium for shoot growth comprising of MS medium supplemented with auxin NAA 0.02-2.0 mg per liter, cytokinin BAP 0.2-2.0 mg per liter, inositol 200-600 mg per liter; incubating the cultures in the growth room with light intensity of about 50-90 mu.mol m.sup.−2s.sup−1 having about 10-20 hours of light daily; at 18-25 degree centigrade of temperature for period of 3-6 weeks, multiplying the cultures in the same medium and same culture conditions, and continuing the multiplication up to 10 cycles or till the vigor of the plant multiplication diminished, transferring the shoots onto medium for rooting comprising of MS medium of 0.1-1.0 strength, and maintaining for 4-6 weeks or till formation of well developed roots; subjecting the in vitro regenerated plants to primary and secondary hardening; transferring the hardened plants to the field which gave about 95% survival in the field conditions. The multiplication ratio achieved by the process is of the order of 1:12-1:20. Due to such high ratio of multiplication the present invention process can be carried out significantly with low cost of production in relatively lesser time.

BRIEF DESCRIPTION OF THE FIGURES

The following figures, which are in the form of coloured photographs are part of the present specification and are incorporated to further demonstrate certain aspects of the present invention. The invention may be better understood by reference to these figures in combination with the detailed description presented herein.

FIG. 1: Shows leaf as an explants with callus formation.

FIG. 2: depicts whole process of micropropagation from nodal explant.

FIG. 2(*a*): shows nodal segment with initiation of bud at nodal region.

FIG. 2(*b*)-(*e*): shows various stages of initiation of shoots.

FIG. 2(*f*)-(*h*): shows shooting and multiplication

FIG. 2(*i*): shows whole regenerated plant with well developed shoot and roots.

Two copies of the figures are forwarded in color and one copy is being submitted in black and white.

DETAILED DESCRIPTION OF THE INVENTION

The present invention describes a novel highly efficient in-vitro system for micro-propagation of rose scented geranium *Pelargonium graveolens* L. Herit of Bourbon or Reunion type for producing a large number of viable plants.

The present invention provides a process for in-vitro micro-propagation of *Pelargonium graveolens* of Bourbon or Reunion type to produce the plants, which are of true to type preserving the genotype of the elite mother plants from which they are derived. Furthermore the present invention provides in-vitro micro-propagation of *Pelargonium graveolens* of Bourbon or Reunion type with high multiplication ratio producing large number of plants rapidly thereby rendering the process cost-effective.

In accordance with the present invention there is provided an identification of the best explant suitable for direct regeneration and with potential to maximum multiple shooting.

In accordance with the present invention there is provided composition of most favorable culture media optimized for the most appropriate growth regulators effective in providing the direct and rapid regeneration, high multiplication of shoot ratio, further proper growth of shoot and formation of well-developed root system.

In accordance with the present invention for in-vitro micro-propagation of *Pelargonium graveolens* of Bourbon or Reunion type, there is provided an identification of optimum culture conditions and procedure for initiation, differentiation, maintenance and healthy growth of cultures and regenerates.

In accordance with the present invention there is also provided both primary as well as secondary hardening of tissue cultured micropropagated plants. The lack of which, could be a major constraint in producing the large number of plants due to the relatively high mortality and loss of the plantlets during this step of process. The present invention establishes the of rooting medium/soil mixtures as well the growth environment in the green house to ensure proper root development which is crucial for the vigor and vitality of the plant and minimize the said losses during hardening. The hardening process involves primary hardening in the green house and the secondary hardening outside the green house. Primary hardening is targeted towards providing optimal conditions for root development like diffused/controlled light penetration, high humidity and conducive temperature. Secondary hardening being outside the green house involves gradual movement of the plants from the partial shade conditions to the natural open environment.

In accordance with the present invention there is provided process for in-vitro system micro-propagation of rose scented geranium *Pelargonium graveolens* L. Herit of Bourbon or Reunion type, the process comprises of the following steps:

i. selecting the healthy elite plants of rose scented geranium *Pelargonium graveolens* L. Herit of Bourbon or Reunion type, with desired oil characteristic or other required feature from the open field condition to serve as mother plant;

ii. treating the selected mother plants growing in the open field condition with systemic fungicides and insecticides in a conventional manner; at one week interval, for four weeks;

iii. transferring the treated mother plants from open field to green house with conditions set at 80-90% relative humidity, 22+.sub.−2° C. temperature, with 50% light cut;

iv. collecting the various explants from mother plants growing in green house conditions for at least 4 months;

v. cleaning the explants;

vi. surface sterilizing the explants;

vii. cutting explants into small pieces of approximately 2-12 mm length or diameter;

viii. inoculating the explants on medium for shoot regeneration and multiplication comprising of modified MS medium supplemented with different concentration of growth hormones selected from auxins like NAA 0.05-5 mg per liter, cytokinins like kinetin 2.5-7.5 mg per liter or BAP 0.15-3 mg per liter, or the like and or combination thereof, inositol 200-400 mg per liter along with various gelling agents selected from agarose, phytagel or the like and or combination thereof in the range of 0.3-1.0%, and source of carbohydrate like glucose, sucrose, or the like and or combination thereof in the range of 0.2-10%;

ix. incubating the inoculated explants for a photoperiod of day ranging from 0-24 hours and night or dark period ranging from 24 -0 hours for period of 2-10 days at a temperature of 18-25 degree centigrade; scoring the incubated plants for contamination if any;

x. relocating the uncontaminated cultures to growth room with light intensity of about 60-80 mu.mol m.sup.−2s.sup−1 having about 10-20 hours of light daily; at 18-25 °C. temperature for at least 3-6weeks to give healthy cultures;

xi. transferring the healthy cultures on the same medium and same culture conditions for the period of 2-4 weeks for further growth, evaluating the explant for their response 2 weeks onwards, in every week;

xii. harvesting the multiple shoots with the healthy growth from the explant with the best growth, the said explant with the best growth being the nodal explants;

xiii. dissecting the multiple shoots into 0.2-1 cm size and transferring to a medium for shoot growth comprising of MS medium supplemented with growth hormones selected form auxins like NAA 0.02-2.0 mg per liter, cytokinins like BAP 0.2-2.0 mg per liter, inositol 200-600 mg per liter, along with various gelling agents selected from agarose, phytagel or the like and or combination thereof in the range of 0.3-1.0%, and source of carbohydrate like glucose, sucrose, or the like and or combination thereof in the range of 0.2-10%;

xiv. incubating the cultures in the growth room with light intensity of about 50-90 mu.mol m.sup.−2s.sup−1 having about 10-20 hours of light daily; at 18-25 degree centigrade of temperature for period of 3-6 weeks, multiplying the cultures in the same medium and same culture conditions, and continuing the multiplication up to 10 cycles or till the vigor of the plant multiplication diminished;

xv. transferring the shoots of 3-6 cm height to medium for rooting comprising of MS medium of 0.1-1.0 strength, and maintaining for 4-6 weeks or till formation of well developed roots, xvi. removing the rooted plants from container, washing with water to remove agar adhering to the plant, drenching with 0.02-0.2% fungicide like bavistin and planting on a soil mixture comprising of pre sterilized red soil, cocopeat and decomposed farm yard into 1:1:1 proportion and keeping in the green house with 70-80% relative humidity, 40-60% of the shade at a temperature of about 18-28 degree centigrade for primary hardening for 3-6 weeks;

xvii. transferring the plants outside the green house under the shade with 15-30% light cut for secondary hardening for 2-6 weeks;

xviii. transferring the hardened plants to the field.

In accordance with the present invention the selected elite plants of rose scented geranium *Pelargonium graveolens* L. Herit of Bourbon or Reunion type growing in an open field are subjected to treatment with systemic fungicides selected from Bavistin, Captan, Dithane, Thiovit, or the like used at a concentration of 0.01-0.1% v/v and insecticides selected from Nuvacron, Fastac, Ultracid 40-WP, Thiodane or the like at a concentration of 0.01-0.1% v/v at one week interval for 4 weeks.

In accordance with the present invention prior to removal of explants from *Pelargonium graveolens* mother plants, they were transferred from open field to green house in controlled environment with condition set at 80-90% relative humidity, 22+.sub.−2° C. temperature with 50% light cut and maintained at least for period of 4 weeks, in order to avoid the systemic microbial contamination and consequential loss of culture.

In accordance with the present invention the explant used is selected from leaf, leaf petiole, stem, stem internode, stem nodal segment, seeds, apical bud, auxiliary bud, or the like from rose scented geranium *Pelargonium graveolens* L. Herit of Bourbon or Reunion type with requisite characteristic either in terms of oil or other desired feature. The preferred explant is stem nodal region.

In accordance with the present invention cleaning of the explant comprises of washing the explants thoroughly under running tap water, washing with 0.01-0.2% Tween-20 for 2-10 minutes, followed by washing with distilled water, treating the explant with disinfectant solution comprising systemic fungicides like bavistin 0.1%, contact fungicide like Indofil M-45 0.1% and systemic insecticide like Fenualerate 0.1%, for 5-10 minutes and repeatedly washing with sterilized distilled water to remove any traces of fungicide & insecticide.

In accordance with the present invention surface sterilization is carried out by treating the clean explant under laminar flow with mercuric chloride 0.01-1% for 2-10 minutes period, followed by multiple washing each for 2 -20 minutes time period with sterile distilled water to remove the left over residues of mercuric chloride.

In accordance with the present invention the medium used for regeneration of shoots and to obtain multiple shooting comprises of Murashige and Skoog (MS) basal medium with source of carbohydrate like glucose, sucrose, or the like in the range of 0.2-10%; gelling agent selected from agar, phytagel or the like in the range of 0.3-1.0%; supplemented with inositol 200-400 mg per liter; growth hormones or additional components. The growth hormone comprised in the medium for regeneration of shoots and multiplication can be selected from auxin like naphthalene acetic acid, naphthaleneacetamide, naphthoxyacetic acid, or the like in the range of 0.05-5 mg per liter; cytokinin like kinetin 2.5-7.5 mg per liter, benzyl adenine 0.2-2 mg per liter or the like and or combination thereof.

It was observed that the use of the inositol in the range of 200-400 mg per liter in the medium for regeneration and multiple shooting was at least in part was contributory factor for giving rise to maximum multiple shooting. Without inositol or addition of the inositol beyond the specified concentration the medium did not give significant multiplication.

In accordance with the present invention the hormones optionally used in addition to those already stated herein in the shoot regeneration and multiplication medium and medium for shoot growth may be selected from auxins or cytokinins or the like at various concentrations. Auxin may be selected from 2,4-Diehlorophenoxyacetic acid, indole acetic acid, indole-3-propionic acid, indole-3-butyric acid, indolepyruvic acid, phenyl acetic acid, phenoxy acetic acid, or the like. Cytokinin may be selected from zeatin z-ip, or the like.

The basal MS medium that is Murashige and Skoog medium used in accordance with the present invention comprises of the following components,

| Components | Concentration (mg/l) |
|---|---|
| Sucrose | 30000 |
| Magnesium sulfate ($MgSO_4$) $7H_2O$ | 370 |
| Calcium chloride ($CaCl_2$ $2H_2O$) | 400 |
| Potassium nitrate ($KNO_3$) | 2000 |
| Ammonium nitrate ($NH_4NO_3$) | 1500 |
| Potassium phosphate ($KH_2PO_4$) | 50 |
| Ferrous sulfate ($FeSO_4$ $7H_2O$) | 30 |
| Sodium ethylenediaminetetraacetic acid ($Na_2$ EDTA) | 30 |
| (Manganese sulfate) $MnSO_4$ $4H_2O$ | 20 |
| Zinc sulfate ($ZnSO_4$ $7H_2O$) | 10 |
| Cupric sulfate ($CuSO_4$ $7H_2O$) | 0.025 |
| Calcium Chloride ($CaCl_2$ $6\ H_2O$) | 0.025 |
| Potassium Iodide (KI) | 0.5 |
| Boric acid ($H_3BO_3$) | 5.0 |
| Molybdic acid sodium salt ($NaMoo_4$ $2H_2O$) | 0.25 |
| Myo-Inositol | 100 |
| Glycine | 2.0 |
| Nicotinic acid | 0.5 |
| Pyridoxine | 0.5 |
| Thiamine Hcl | 1.0 |

The multiplication ratio obtained with the present invention process was as high as 1:12 to 1:20. Thus the present invention provides very rapid and efficient and method for multiplication of rose scented geranium *Pelargonium graveolens* L. Herit of Bourbon or Reunion type and at the same time significantly lowers the production costs of commercial propagation of the said species.

The present invention can be useful for,
multiplication of an elite variety with high quality essential oil required in perfumes, cosmetics or for therapeutic purposes.
modulating the production of secondary metabolites;
development of basic protocol for efficient regeneration, which form the very basis of further plant transformation research.
As defined herein NAA is α-naphthalene acetic acid.
As defined herein IAA is Indole acetic acid
As defined herein BA is 6-Benzyladenine
As defined herein BAP is Benzyl amino purine As defined herein MS medium is Murashige and Skoog's (MS) medium comprising of components of Murashige and Skoog's basal medium as defined in terms of their chemical composition and concentration.

The following examples are given by way of the illustration of the present invention. These examples should not be construed as limiting to the scope of the present invention.

EXAMPLES

Example 1

Identification of Explant:

According to the present invention to identify the explant with best regeneration and multiplication capacity, following experiment was conducted, Various explants namely leaf, stem, petiole and nodal segment were excised from the rose scented geranium *Pelargonium graveolens* L. Herit of Bourbon or Reunion type plants growing in controlled environment in the green house at least for period of 4 months. The explants were cleaned by washing with mild detergent like Tween-20 0.1% for 5 minutes, followed by washing with distilled water. In order to remove the fungus or bacterial contaminants from the surface of the explants they were washed with disinfectant solution containing systemic fungicide bavistin 0.1%, contact fungicide Indofil M-45 0.1%, systemic insecticide Fenualerate 0.1% and after each wash they were rinsed with distilled water to remove fungicide and insecticide. The explants were surface sterilized by treating the explant under laminar flow with mercuric chloride solution 0.01% for 6 minutes period, followed by multiple washing each for 5 minutes time period with sterile distilled water to remove the left over residue of mercuric chloride. The explants were then cut into small pieces of 6 mm length or diameter. The explants after dipping into double distilled water placed onto the medium for shoot regeneration and multiplication with the help of sterilized forceps in laminar flow. The medium for shoot regeneration and multiplication consisted of MS medium modified to have 400 mg per liter of inositol along with 7.5 mg per liter of kinetin and 1 mg per liter of Naphthalene acetic acid for nodal explant and MS medium modified to have 400 mg per liter of inositol along with 1 mg per liter of BAP and 0.1 mg per liter of Naphthalene acetic acid for leaf explant. Cultures were initially incubated in photoperiod of 24 hours of dark period at a temperature of 18-25 degrees centigrade for the period of 8 days. The culture tubes were transferred to growth room with light intensity of about 70 mu.mol m.sup.−2s.sup−1. and about 16 hours of light daily. Cultures were maintained for 3 weeks period to observe the relative regeneration of shoot and multiplication capacity of different explants cultured on the same medium and same condition. In case of leaf as explant induction of callus was observed which eventually differentiated into shootlets. Culturing of nodal segments gave the healthy multiple shooting at the nodal region, wherein the multiplication ratio was as high as 1:16. Thus the use of leaf as an explant for development of true to type resultant plants was eliminated due to the formation of callus at initial stage, which could give rise to somaclonal variants. The stem nodal regions proved to be the best explant.

Example 2

Nodal region explants were collected from rose scented geranium *Pelargonium graveolens* L. Herit of Bourbon or Reunion type growing in controlled environment in the green house at least for period of 4 months. Nodal explants were washed with distilled water, followed by 0.1% of Tween-20 for 5 minutes and final wash with distilled water. The explants were treated with a disinfectant solution comprising bavistin 0.1%, Indofil M-45 0.1% and Nuvacron 0.1%, for 10 minutes and repeatedly washed with sterilized distilled water each lasting for 5 minutes.

The explants were then sterilized under laminar flow with 0.01% mercuric chloride for five minutes, followed by washing with sterilized distilled water for 5 times each lasting for 5 minutes to ensure that there is no residual left over of mercuric chloride on the surface of explants. Nodal explants were cut with the help of sterilized scalpel into size of about 5 mm under laminar flow, after dipping into sterilized water, with the help of forceps, were then placed onto medium for shoot regeneration and multiplication comprising of Murashige & Skoog basal medium supplemented with sucrose 3% w/v and agar 0.8% w/v, inositol 400 mg per liter, kinetin 5 mg per liter and 1 mg per liter of Naphthalene acetic acid. The cultures were incubated at 22.+-0.3 degree. C. in 24 hours of dark and 0 hour of day light period for one week period and scored for contamination if any. Uncontaminated cultures were transferred to growth room with 25.+-0.2 degree. C. temperature, 70 mu.mol m.sup.-2s.sup.-1. light and 16 hours of light daily. The cultures were maintained till multiple shoots were formed. These healthy multiple shoots if required were transferred to same medium and maintained under same condition for 3-6 weeks.

The healthy multiple shoots were taken out and cut into size of about 5 mm and transferred to medium for shoot growth comprising of MS medium supplemented with inositol 500 mg per liter, BAP 1 mg per liter and NAA 0.2 mg per liter and incubated in the growth room with light of 70 mu.mol.m.sup.-2s.sup-1 intensity, 16 hours of photoperiod and 22.+-0.3 degree. C. temperature for period of 3 weeks. Cultures were multiplied on the same medium and in same culture conditions till 10 cycles or till the vigor of plant multiplication diminished.

The shoots of 3-4 cm size were taken out and transferred to Murashige & Skoog medium of 0.25 strength for rooting and maintained till formation of well-developed root system.

Rooted plants were taken out from the containers and washed with water to remove any agar attached to the plants. The plants were drenched with bavistin 0.1% and planted in a soil mixture containing pre sterilized red soil, cocopeat and decomposed farm yard in the ratio of 1:1:1 and kept in a green house with 70% relative humidity. 50% of the light shade and temperature of 22.+-0.3 degree. C. for primary hardening for 4 weeks.

Following primary hardening the plants were transferred outside the green house with 25% light cut for 4 weeks for secondary hardening.

Plants with 6-8 cm height or with 4-6 leaves after secondary hardening were transferred to field under drip irrigation.

Example 3

Micropropagation of rose scented geranium *Pelargonium graveolens* L. Herit of Bourbon or Reunion type was carried out as per the method illustrated in example 2, as a whole, except for the medium for shoot regeneration and multiplication, wherein the composition contained MS medium modified to have 400 mg per liter of inositol, 7 mg per liter of kinetin and 1 mg per liter of Naphthalene acetic acid.

Example 4

Micropropagation of rose scented geranium *Pelargonium graveolens* L. Herit of Bourbon or Reunion type was carried out as per the method illustrated in example 2, as a whole except for the composition of medium for shoot growth which contained MS medium supplemented with inositol 500 mg per liter, 6-Benzylaminopurine 1 mg per liter and Naphthalene acetic acid 0.1 mg per liter.

Example 5

Micropropagation of rose scented geranium *Pelargonium graveolens* L. Herit of Bourbon or Reunion type was carried out as per the method illustrated in example 2, except for the composition of shoot regeneration and multiplication medium, which, was similar to that in example 3 and rooting medium, which contained Murashige & Skoog medium of 0.4 strength.

Example 6

Micropropagation of rose scented geranium *Pelargonium graveolens* L. Herit of Bourbon or Reunion type was carried out as per the method illustrated in example 2, except for the composition of shoot regeneration and multiplication medium, which, was similar to that in example 3 and rooting medium, which contained Murashige & Skoog medium of 0.5 strength.

Example 7

Micropropagation of rose scented geranium *Pelargonium graveolens* L. Herit of Bourbon or Reunion type was carried out as per the method illustrated in example 2, except for the composition of shoot regeneration and multiplication medium, which, was similar to that in example 3 and medium for shoot growth was similar to that in example 4 and rooting medium was similar to that in example 6.

Various modifications of the present invention in addition to those described and illustrated herein will be apparent to those skilled in the art from the foregoing description and examples. Such modifications are also intended to fall within the scope of the appended claims.

We claim:

1. A method for an efficient in-vitro system of micropropagation of rose scented Geranium, *Pelargonium graveolens* L. Herit of Bourbon type of Reunion origin for producing a large number of viable in-vitro plants from explants with a multiplication ratio of 1:15-1:20, the said method comprising the steps of:
   i. treating mother plants growing in open field conditions with systemic fungicides and insecticides in a conventional manner, at one week intervals, for four weeks;
   ii. selecting a mother plant from healthy elite plants of rose scented geranium *Pelargonium graveolens* L. Herit of Bourbon or Reunion type from the mother plants, having a desired oil characteristic from open field conditions as the mother plant grown in an open field;
   iii. transferring the treated mother plant from the open field conditions to a green house with green house conditions set at 80-90% relative humidity, 22+.sub.-2° C. temperature, with 50% light cut;

iv. selecting and collecting nodal explants with a small multiplication ratio of 1:15-1:20 from the mother plant growing in the green house conditions for 4 months;
v. cleaning the nodal explants;
vi. surface sterilizing the nodal explants;
vii. cutting the nodal explants into small pieces of approximately 2-12 mm length or diameter;
viii. inoculating the small pieces of nodal explants on a shoot regeneration and multiplication media for shoot regeneration and multiplication comprising modified MS media supplemented with 200-400 mg of inositol per liter, growth hormones selected from the group consisting of auxins like NAA 0.05-5 mg per liter, cytokinins like kinetin 2.5-7.5 mg per liter and BAP 0.15-3 mg per liter to produce shoot cultures of inoculated nodal explants;
ix. incubating the inoculated nodal explants for a photoperiod of a day ranging from 0-24 hours and a night or a dark period ranging from 24-0 hours for a period of 2-10 days at a temperature of 18-25 degrees centigrade, scoring the incubated shoots of the inoculated nodal explants to produce cultures free of contamination if any, separating uncontaminated cultures from contaminated cultures;
x. relocating the uncontaminated cultures of nodal explants and keeping them in a growth room wherein illumination is provided and the illumination has a light intensity of about 50-90 mu.mol m.sup.−2s.sup−1 and provided for a duration of about 10-20 hours of light daily, at a temperature of 18-25° C. for at least 3-6 weeks to produce healthy cultures of nodal explants;
xi. transferring the healthy cultures of nodal explants on the same media and same culture conditions of shoot regeneration and multiplication, for a period of 2-4 weeks for further growth into multiple healthy shoots, and evaluating them to select the healthy multiple shoots from the nodal explants;
xii. harvesting the healthy multiple shoots;
xiii. dissecting the healthy multiple shoots into 0.2-1 cm segments and transferring to media for shoot growth comprising an MS media supplemented with 200-600 mg inositol per liter, growth hormones selected from the group consisting of auxins such as NAA 0.02-2.0 mg per liter, and cytokinins such as BAP 0.2-2.0 mg per liter;
xiv. incubating cultures from the healthy multiple shoots in the growth room wherein lighting is provided having a light intensity of about 50-90 mu.mol m.sup.−2s.sup−1 and providing illumination for a period of about 10-20 hours of light daily; at 18-25 degree centigrade of temperature for a period of 3-6 weeks, multiplying the cultures-from the healthy multiple shoots in the same media and the same culture conditions, and continuing the multiplication up to 10 cycles or until the vigor of plant multiplication is diminished;
xv. transferring the healthy multiple shoots of 3-6 cm height on to media for rooting comprising MS media of 0.1-1.0 strength, and maintaining for a period of 4-6 weeks or until formation of well developed rooted plants;
xvi. removing the rooted plants from a container, washing the rooted plants with water to remove agar adhering to the rooted plants, drenching with 0.02-0.2% fungicide like Bavistin and planting on a soil mixture comprising pre-sterilized red soil, cocopeat and decomposed soil from a farm yard into 1:1:1 proportion and keeping them in a green house with 70-80% relative humidity, shaded 40-60% at a temperature of about 18-28 degrees centigrade for primary hardening for 3-6 weeks;
xvii. transferring the rooted plants outside of the green house under shade with 15-30% light cut for secondary hardening for 2-6 weeks; and
xviii. transferring the hardened rooted plants to an open field.

2. The method, according to claim 1, wherein the systemic fungicides used for the treatment of *Pelargonium graveolens* plants growing in the open field is, Bavistin, Captan, Dithane, Thiovit, or the like used at a concentration of 0.01-0.1% v/v.

3. The method, according to claim 1, wherein the insecticides used for the treatment of the field grown *Pelargonium graveolens* plants are selected from the group consisting of Fenualerate, Nuvacron, Fastac, Ultracid 40-WP, and Thiodane, used at a concentration of 0.01-0.1% v/v.

4. The method, according to claim 1, wherein the explants are selected from the group consisting of leaf, leaf petioles, stem, stem internodes, stem nodal regions, seeds, apical buds, and auxillary buds.

5. The method, according to claim 1, wherein the cleaning of the nodal explants comprises washing the nodal explants thoroughly under running tap water, washing with 0.01-0.2% Tween −20 for 2-10 minutes, followed by washing with distilled water, treating the nodal explants with a disinfectant solution comprising the systemic fungicides such as Bavistin 0.1 %, contact fungicide such as Indofil M-45 0.1% and systemic insecticide such as Fenualerate 0.1%, for 5-10 minutes and repeatedly washing with sterilized distilled water.

6. The method, according to claim 1, wherein the sterilization comprises treating the clean nodal explant under laminar flow with mercuric chloride 0.01-1% for 2-10 minutes period, followed by multiple washing with sterile distilled water, each lasting for a period of 2 -20 minutes.

7. The method, according to claim 1, wherein the auxin, NAA in the shoot regeneration and multiplication media are present in the range of 0.05-0.15 mg per liter.

8. The method, according to claim 1, wherein the cytokinin, kinetin in shoot regeneration and multiplication media are present in the range of 4-7 mg per liter.

9. The method, according to claim 1, wherein the cytokinin, BAP in shoot regeneration and multiplication media are present in the range of 0.5-2 mg per liter.

10. The method, according to claim 1, wherein the auxin, NAA in media for shoot growth are present in the range of 0.05-0.5 mg per liter.

11. The method, according to claim 1, wherein the cytokinin, BAP in media for shoot growth are present in the range of 0.5-1 mg per liter.

12. The method, according to claim 1, wherein the shoot regeneration and multiplication media and the media for shoot growth may optionally further comprise an additional auxin selected from the group consisting of 2,4-Dichlorophenoxyacetic acid, phenyl acetic acid, phenoxy acetic acid, indole-3-propionic acid, indole-3 -butyric acid, indole-pyruvic acid, naphthoxy acetic acid, naphthalene acetic acid, and indole acetic acid.

13. The method, according to claim 1, wherein the shoot regeneration and multiplication media and hormones optionally used in the shoot regeneration and multiplication media for shoot growth may optionally further comprise additional cytokinin selected from the group consisting of zeatin and z-ip.

14. The method, according to claim 1, wherein the shoot regeneration and multiplication media and for shoot growth further comprises treating gelling agents selected from the group consisting of agarose and phytagel in the range of 0.3-1.0%, and a source of carbohydrate selected from the group consisting of glucose and sucrose, in the range of 0.2-10%.

15. The method, according to claim 1, wherein the MS media for the rooting have a concentration strength of 0.25-0.75.

16. The method according to claim 1, wherein the explant is selected from a leaf.

17. The method according to claim 1, wherein the explant is selected from a leaf petiole.

18. The method according to claim 1, wherein the explant is selected from a stem nodal region.

* * * * *